United States Patent [19]

Horsfield et al.

[11] 4,211,881
[45] Jul. 8, 1980

[54] PREPARATION OF PHTHALIC ACID BY SINGLE STEP CONTINUOUS AIR OXIDATION OF LIQUID ORTHO-XYLENE

[75] Inventors: Sydney G. Horsfield, Wheaton; George E. Kuhlmann; Alan G. Bemis, both of Naperville, all of Ill.

[73] Assignee: Standard Oil Company (Indiana), Chicago, Ill.

[21] Appl. No.: 961,763

[22] Filed: Nov. 17, 1978

[51] Int. Cl.$^2$ .............................................. C07C 51/33
[52] U.S. Cl. ..................................................... 562/416
[58] Field of Search ......................................... 562/416

[56] References Cited

U.S. PATENT DOCUMENTS

| | | | |
|---|---|---|---|
| 2,858,334 | 10/1958 | Landau | 562/416 |
| 3,920,735 | 11/1975 | Wampfler | 562/416 |

*Primary Examiner*—Alan Siegel

*Attorney, Agent, or Firm*—Fred R. Ahlers; William T. McClain; William H. Magidson

[57] ABSTRACT

This invention relates to the neat air oxidation of liquid o-xylene in a continuous manner in a single step to overcome the limited conversion of the process of British Patent Specification No. 856,245 or of the process of U.S. Pat. No. 3,920,735. More specifically this invention overcomes the limited conversion of o-xylene by its single step air oxidation in the presence of catalysis provided by ions of cobalt, manganese and bromine not only by maintaining the proper relationship of temperature, pressure and free water concentration in the reaction mixture to minimize the conversion of o-phthalic acid to its intramolecular anhydride but also by conducting the oxidation in the presence of small amounts of acetic or benzoic acid to make miscible the otherwise immiscible liquid phases of liquid o-xylene and liquid o-phthalic acid containing components of catalysis and free liquid water.

6 Claims, No Drawings

PREPARATION OF PHTHALIC ACID BY SINGLE STEP CONTINUOUS AIR OXIDATION OF LIQUID ORTHO-XYLENE

BACKGROUND ART

U.S. Pat. No. 2,833,816 disclosed the unique catalysis provided by the combination of a source of bromine with one or more metal oxidation catalyst for oxidizing with a source of molecular oxygen gas (e.g., air) all the alkyl-substitutents of alkyl-substituted aromatic hydrocarbons to an aromatic di-, tri- or higher polycarboxylic acid (e.g. oxidation of a xylene to a phthalic acid) under liquid phase conditions. Since such disclosure, there has been an interest shown from time to time for the use of said catalytic liquid phase oxidation for the conversion of o-xylene to the anhydride of o-phthalic acid.

For example, U.S. Pat. No. 3,402,184 disclosed a continuous process for oxidizing o-xylene in an acetic acid solution containing ions of cobalt, manganese and bromine with air in three steps. Such o-xylene oxidation results in a solution of phthalic anhydride ("PAN") in the acetic acid. Said solution of PAN is combined with water and heated to convert the dissolved PAN to insoluble o-phthalic acid product.

British Patent Specification No. 856,245 published in 1960 discloses that a single step, neat (no extraneous solvent) oxidation of o-xylene does not go beyond 70 mole percent conversion of the xylene to phthalic anhydride but a combination of fresh xylene and the 30 percent unoxidized cannot be oxidized.

U.S. Pat. No. 3,920,735 discloses that the neat, single step oxidation of o-xylene with air in the presence of cobalt, manganese, zirconium and bromine produces a 60 mole percent yield of phthalic acid together with 0.97 mole percent yield of o-toluic acid, 2.95 mole percent yield of phthalide and 1.88 mole percent yield of 2-carboxybenzaldehyde. Such a PAN product is quite impure and contains a relatively large amount of difficulty removable phthalide.

Lastly, copending U.S. Pat. application Ser. No. 867,050, filed Jan. 5, 1978 describes an improved neat oxidation of o-xylene in the liquid phase to 85 to 92 mole percent yields of o-phthalic acid. The key to such substantially higher yield is to maintain the o-xylene oxidation product as the free dicarboxylic acid; that is, o-phthalic acid, and avoid conditions which permit such acid to dehydrate to its intramolecular anhydride, PAN. Such conditions are the conduct of the neat oxidation of liquid o-xylene with air at a temperature in the range of from 150° C. up to 235° C., at a gauge pressure of from 17 up to at least 28 kg/cm² and in the presence of from 2 up to 7 weight percent water in the reaction mixture. Satisfactory rates of oxidation are, under those conditions, obtained in the presence of catalysis provided on the basis of one gram mole of o-xylene by from 0.3 up to 10 milligram atoms of cobalt, from 0.15 up to 20 milligram atoms of manganese and from 0.225 to less than 60 milligram atoms of bromine. That is, the ratio of gram atoms of bromine per gram atom total of cobalt and manganese is at least 0.5:1 but is less than 2:1. Also, when the cobalt concentration is less than 0.75 milligram atom per gram mole of o-xylene than the difference between the actual cobalt concentration and the 0.75 milligram atom per gram mole of o-xylene can be supplied by zirconium on a gram atom for gram atom basis even though zirconium is not a polyvalent transition metal.

Said higher conversion and yield performing process is illustrated by and is limited to the use of batchwise or semi-continuous operation. By "semi-continuous" operation is meant the type of operation wherein a continuous mode of simultaneously charging air and o-xylene follows the first batchwise mode of charging all of the components of catalysis and water and heating the same to reaction temperature under reaction pressure, at the completion of charging all the xylene continuing only the charging of air until for all practical purposes the consumption of oxygen ceases and then stopping the air, and discharging all the reaction mixture for processing to recover the o-phthalic acid product. Heating to reaction temperatures of the mixture of water and components of catalysis can be accomplished by heat of reaction released by oxidizing 5 to 25% of the o-xylene added with said mixture.

The simple batchwise and the semi-continuous operations of the above copending patent application both provide liquid reaction products containing 89 to 92 weight percent o-phthalic acid. Said simple batchwise operation produces o-phthalic acid in yields of up to 92 mole percent and consumes 5.5 mole percent of o-xylene by total combustion as determined by measurement of the total oxides of carbon produced. Said semi-continuous operation results in an 85 mole percent yield of o-phthalic acid and a 9.7 mole percent total combustion of o-xylene.

The results of said semi-continuous neat air oxidations of o-xylene demonstrate that operating conditions were found to overcome the yield limitation problem of single step oxidation mentioned in British Pat. No. 856,249. Also, from the results of said semi-continuous neat air oxidation of o-xylene one would assume that its operating conditions were applicable for successful operation of truly continuous operation with perhaps the added disadvantage of a higher (above 9.7) mole percent total combustion of o-xylene.

However, such assumption was found not to be correct. Because of the continuous addition of fresh xylene and components of catalysis with the requisite free water and the continuous removal of part of the reaction mixture, continuous operation produces a reaction mixture always containing unreacted xylene. Such difference is in contrast to the batchwise or semicontinuous operations whose reaction mixtures always have a diminishing o-xylene concentration before the reaction mixture is withdrawn from the site of reaction. Such difference in composition of reaction mixture is material because it gives rise to a problem interfering with successful continuous one step oxidation not found during the development of the successful one-step operation by batchwise or semi-continuous operation. Manifestation of said problem arising from the presence of unreacted o-xylene begins, we found, when the liquid reaction mixture contains 40 to 41 weight percent o-phthalic acid. Upon reaching such composition there forms a liquid o-xylene phase and a liquid o-phthalic acid phase which contains the components of catalysis and the requisite 2 to 7 weight percent free water. Said two liquid phases, we found, were immiscible even though the reaction mixture was vigorously stirred. Because the components of catalysis are in the liquid o-phthalic acid phase, the catalysis is not effectively available for rapid oxidation of o-xylene and it accumulates as an increasing immiscible liquid phase. Up to reaching the 40 to 41 weight percent o-phthalic acid concentration the oxidation reaction is vigorous but, as the immiscible liquid o-xylene accumulates, the oxidation reaction diminishes in vigor until the rate of oxidation becomes commercially unacceptable. Such vigor diminishing condition is readily observable from the volume ratio of o-xylene to water condensed from the exhausted from the oxidation zone. Such volume ratio is normally in the range of from 0.3:1.0 to 0.5:1.0 but the reaction's diminishing vigor is indicated by change of such ratio to 1:1 and finally to 2:1 for an unacceptable reaction rate.

Even when the o-phthalic acid concentration reached 40–41 weight percent in the batchwise and semi-continuous oxidation there was, it is submitted, sufficient benzoic and o-toluic acid present in the reaction mixture to make miscible the o-xylene and the liquid o-phthalic acid solution of water and catalyst components.

We have, however, discovered a simple solution to said problem of forming two immiscible liquid phases. Said solution comprises the essential feature of the present inventive contribution to the continuous single step oxidation of o-xylene with substantially complete conversion thereof to o-phthalic acid yields of 90 mole percent and with total combustion of o-xylene of less than 9 mole percent.

SUMMARY OF THE INVENTION

The unique problem of formation of two immiscible liquid phases can be avoided according to the present invention by conducting the one step neat oxidation of liquid o-xylene continuously in the presence of from 5 up to 20 grams of acetic acid or liquid benzoic acid per gram mole of o-xylene.

Such use of acetic acid or liquid benzoic acid can be made by the separate addition of said acid to the stirred reaction zone simultaneously with the addition of a source of molecular oxygen gas, o-xylene and an aqueous solution of components of catalysis, or by using the acetic or liquid benzoic acid as solvent carrier of the components of catalysis and the requisite water, or in the case of using benzoic acid, to predissolve it in the o-xylene fed to the stirred oxidation zone. Not only does such use of acetic or benzoic acid avoid the formation of two immiscible liquid phases, but the use of said miscibility assisting acid also negates the need to use zirconium in combination with cobalt when the latter's concentration is from 0.5 up to 0.75 milligram atom per gram mole of o-xylene and makes the reaction more tolerant of higher water, above 7 weight percent concentrations in the reaction mixture. As will be later demonstrated the use of such acid as miscibility aid makes possible the successful one step continuous neat oxidation of o-xylene even when the liquid reaction mixture contains up to 20 weight percent water.

While acetic acid and benzoic acid do suppress the total combustion of o-xylene, acetic acid suppresses such total combustion at the sacrifice of 50% of the acetic acid to its total combustion. The neat oxidation of o-xylene does produce some small amount of benzoic acid, less than 1.0 mole percent of the xylene. Since benzoic acid suppresses total combustion of o-xylene without itself being more than slightly consumed by total combustion, and since benzoic acid must be removed from the reaction mixture, it is preferred to use benzoic acid as the miscibility aid according to the present invention.

The operating parameters of the present inventive continuous process for the oxidation of o-xylene to o-phthalic acid are an oxidation zone temperature in the range of 200° C. up to 235° C. and gauge pressure in the range of from 23 up to 31 kg/cm$^2$; a water concentration of from 2 up to 21 weight percent in the liquid reaction mixture in the stirred oxidation zone; the use of 5 up to 20 grams of acetic or benzoic acid per gram mole of o-xylene; the use of air, air enriched with oxygen or molecular oxygen gas in amount related to o-xylene charged so that the exhaust from the oxidation zone contains at least one volume percent oxygen; and the use of the components of catalysis per gram mole of o-xylene in the range of from 0.5 up to 10 milligram atoms of cobalt, of from 0.15 up to 20 milligram atoms of manganese, and from 0.225 to less than 60 milligram atoms of bromine.

For the sake of convenience with respect to the use of benzoic acid as the preferred miscibility aid the solubility of benzoic acid in 100 grams of o-xylene is: 7.5 grams of benzoic acid at 25° C., 10 grams of benzoic acid at 30° C. and 20 grams of benzoic acid at 52° C.

The oxidation reaction vessel used in the following catalytic liquid phase neat oxidations of liquid o-xylene with air is of the stirred tank type and has an internal diameter of 15 cm, a height of 76 cm. and a total internal volume of 14 liters. The vessel is constructed of 9.5 mm thick titanium. The reaction vessel has an internal coil which can be used to either supply heat to the stirred liquid contents or to remove heat therefrom by indirect heat exchange between a fluid pumped through said coil and the stirred liquid reaction mixture. The vessel has valved inlets for introducing o-xylene, catalyst solution and one other liquid through flow meters into the upper portion of the vessel, a valved gas inlet for introducing compressed air into the bottom of the stirred reaction mixture, a heat treated valved outlet in the lower portion of the stirred reaction mixture for its withdrawal from the vessel, and a gas outlet in the upper portion of the vessel for withdrawal of exhaust comprising spent air, carbon oxides, water vapor and xylene vapor from the oxidation vessel.

As auxillary apparatus for the oxidation, there are interconnected a first vertical upflow condenser and a second upflow vertical condenser for series flow therethrough of exhaust gas transferred from its outlet in the oxidation vessel to the bottom inlet of the first vertical condenser. Said first vertical upflow condenser has a mean heat exchange area of 0.67 m$^2$ and said second vertical condenser has a mean heat exchange area of 0.39 m$^2$. An adjustable pressure control valve is in the gas exit line from the second vertical condenser and said valve is set to control the pressure in the oxidation vessel and the above condensation system. The two condensers each have their own cooling system of cool water or steam which can be supplied at a gauge pressure of from 0 up to 9 kg.cm$^2$. The decompressed exhaust gas substantially free of water and xylene is cooled to remove any remaining water and xylene and then flows to a wet gas test meter with a flow measuring capacity of 13,590 normal liters per hour. Following said meter there are gas sampling lines leading to $CO_2$, CO and $O_2$ analyzers prior to venting the exhaust to the atmosphere.

Thermowells are provided for measurement of temperature of the stirred reaction mixture, and the gas vented from each of the first and second vertical upflow condensers. The temperature of liquid reflux flowing back to the reaction vessel from the condensers is also measured.

The neat oxidations of liquor o-xylene to follow are of four types: (i) use of water solution of components of catalysis as comparative examples and the examples illustrating the present invention; (ii) use of water solution of components of catalysis and addition of acetic acid; (iii) acetic acid solution of components of catalysis; and (iv) water solution of components of catalysis and benzoic acid dissolved in the o-xylene feed.

The water solution of components of catalysis is prepared by dissolving in each 1.0 liter of water 230.4 grams of cobaltous acetate tetrahydrate, 486 grams of manganous acetate tetrahydrate and 107.2 grams of hydrobromic acid containing 48 weight percent hydrogen bromide. Such solution amounts to 1.52 liters per 1.0 liter of water used and contains the following weight percent of the indicated component.

TABLE I

| Component | Weight percent |
|---|---|
| Cobalt, as element | 2.98 |
| Manganese, as element | 5.96 |
| Bromine, as element | 2.98 |
| Water | 69.3 |

Such solution can be fed at the rate of 8.64 milliliter per gram mole of o-xylene and will furnish 5.39 milligram atoms of cobalt, 11.6 milligram atoms of manganese and 3.98 milligram atoms of bromine per gram mole of o-xylene. The above solution can be modified by increasing its components' concentration by 50% and such solution can be stored at temperatures as low as 20° to 22° C. without the formation of precipitates.

The acetic acid solution of components of catalysis is prepared by dissolving in each liter of acetic acid 115.2 grams of cobaltous acetate tetrahydrate, 243 grams of manganous acetate tetrahydrate and 230.4 grams of hydrobromic acid containing 48 weight percent hydrogen bromide. Such solution amounts to 1.497 liters per 1.0 liter of acetic acid used and contains the following weight percent of the indicated component.

TABLE II

| Component | Weight percent |
|---|---|
| Cobalt, as element | 1.67 |
| Manganese, as element | 3.33 |
| Bromine, as element | 6.67 |
| Acetic acid | 64.0 |
| Water | 13.7 |

To successfully dissolve said amounts of metal salts in the acetic acid, a higher ratio of HBr to metal salt must be used and the mixture: metal salts and hydrobromic acid, is heated to 65° C. before slowly adding the acetic acid. The component concentration can be increased by 50% before a precipitate will form at 20° to 22° C. Precipitation wil also occur when the ratio of bromine to total metals is decreased below the ratio indicated above.

Use of 16.8 milliliters of the above solution containing the concentrations of components indicated in TABLE II for each gram mole of o-xylene will provide 5.2 milligram atoms of cobalt, 11.14 milligram atoms of manganese and 15.35 milligram atoms of bromine per gram mole of o-xylene.

With the use of the aqueous solution of components of catalysis shown in TABLE I at 8.64 milliliters of solution per gram mole of o-xylene there can be used from 5 up to 25 milliliters of 97 to 100% acetic acid to function as the miscibility aid to avoid the formation of two immiscible liquid phases in the oxidation zone.

In Table III to follow, there is given the pertinent operating information for a number of neat oxidations of liquid o-xylene conducted before our discovery of the formation of the two immiscible liquid phases and the solution to that problem. Such oxidations are conducted using o-xylene of a purity above 99 mole %, at reaction temperature between 210° C. and 221° C., at a gauge pressure of 24.6 kg/cm$^2$ unless otherwise indicated, using an air rate of 604 n liters per gram mole of o-xylene, and using the water solution of components of catalysis of TABLE I at the rate of 8.64 milliliters per gram mole of o-xylene. The o-phthalic acid content of the reaction mixture is the weight percent of said phthalic acid on a water-free basis.

TABLE III

| Conditions | Comparative Examples[3] | | | | |
|---|---|---|---|---|---|
|  | I | II | III | IV | V |
| o-Xylene Feed Rate, g. moles/hr | 10.7 | 10.3 | 6.85 | 6.85 | 8.57 |
| Water, wt. % Reaction mixture | <1 | <1 | 2 | <1 | 8 |
| [1]Vent Gas Temperature, °C. | 133 | 138 | 132 | 121 | 118 |
| [2]O$_2$ Content of Exhaust, vol. % | 13 | 11 | 10 | 13 | 11 |
| Condensate xylene/water, vol. ratio | 1.4 | 1.6 | 1.6 | 1.8 | 2.0 |
| Residence Time, minutes | 130 | 135 | 112 | 112 | 90 |
| REACTION MIXTURE: |  |  |  |  |  |
| o-Phthalic Acid, wt. % | 70.7 | 71.1 | 72.0 | 69.1 | 70.0 |

[1]Temperature of gas mixture discharged from second vertical upflow condenser.
[2]Oxygen content is on water free gas.
[3]Oxidation zone gauge pressure is 28.1 kg/cm$^2$ and temperature is between 221° and 232° C.

As the above data indicate, the yield of o-phthalic acid as indicated by the weight percent o-phthalic acid in the reaction mixture is not significantly changed either by increasing the residence time by 25 to 50% or by changing the water content of the reaction mixture. However, a significant increase in o-phthalic acid yield is achieved by modifying the oxidation process of the foregoing comparative examples by the use of acetic acid or benzoic acid according to the present invention.

The effect of the use of acetic acid or benzoic acid is shown in the illustrative examples whose pertinent conditions in addition to those of the comparative examples are shown in TABLE IV to follow. Such illustrative oxidations are conducted at a gauge pressure of 24.6 kg/cm$^2$, the indicated temperature, 604 n liters of air per gram mole of o-xylene, 8.64 milliliters of the water solution of components of catalysis (TABLE I) per gram mole of o-xylene and the amount of acidic or benzoic acid shown.

In Illustrative Examples III and IV the benzoic acid is dissolved in xylene at 65° C. and 95° C., respectively, and the solution was fed at such temperature.

TABLE IV

| Conditions | Illustrative Examples | | | |
|---|---|---|---|---|
|  | I | II | III | IV |
| o-Xylene Feed Rate, g. moles/hr | 7.71 | 7.71 | 8.57 | 8.57 |
| Acetic Acid (Benzoic Acid)[4] | 13.6 | 13.6 | (10.6) | (21.2) |
| Water, wt. % Reaction Mixture | 10 | 10 | 14 | 10 |
| Reaction Temperature, °C.[5] | 221– | 221– | 216– | 221– |

TABLE IV-continued

| | Illustrative Examples | | | |
|---|---|---|---|---|
| Conditions | I | II | III | IV |
| | 232 | 227 | 227 | 232 |
| Vent Gas Temperature °C. | 125 | 116 | 102 | 120 |
| O$_2$ Content of Exhaust, vol. % | 8 | 12 | 12 | 11 |
| Condensate Xylene/Water, vol. ratio | 0.3 | 0.4 | 0.5 | 0.3 |
| Residence time, minutes | 100 | 100 | 90 | 90 |
| Reaction Mixture: | | | | |
| o-Phthalic Acid, wt. % | 92 | 94 | 85.4 | 78.9 |

(4)Acetic Acid (Benzoic Acid) in grams per gram mole of o-xylene.
(5)Reaction temperature in minimum-maximum.

In the next six illustrative examples in TABLE V to follow the acetic acid solution of components of catalysis (TABLE I) is used at the ratio of 16.8 milliliters per gram mole of o-xylene otherwise the reactions are carried out at a gauge pressure of 24.6 kg/cm$^2$, the temperature between 220° C. minimum and 232° maximum and an air rate of 604 n liters per gram mole of o-xylene. Also, in the conduct of Illustrative Example 6 water was added in an amount of 4.9 milliliters to the 16.8 milliliters of catalyst to make the water added with the catalyst comparable to that of Comparative Examples I to IV.

TABLE V

| | Illustrative Examples | | |
|---|---|---|---|
| Conditions | V | VI | VII |
| Xylene Feed Rate, g. moles/hr | 7.28 | 7.28 | 6.42 |
| Water, wt. % Reaction Mixture | 9 | 21 | <1 |
| Vent Gas Temperature, °C. | 131 | 131 | 116 |
| O$_2$ Content of Exhaust, vol. % | 10 | 10 | 9 |
| Condensate Xylene/H$_2$O, vol. ratio | 0.8 | 0.5 | — |
| Residence time, min. | 106 | 106 | 115. |
| Reaction Mixture: | | | |
| o-Phthalic Acid, wt. % | 84 | 94 | 91.4 |

| | Illustrative Examples | | |
|---|---|---|---|
| Conditions | VIII | IX | X |
| Xylene Feed Rate, g. moles/hr | 9.0 | 18.4 | 18.0 |
| Water, wt. % Reaction Mixture | 12 | <1 | <1 |
| Vent Gas Temperature, °C. | 114 | 125 | 126 |
| O$_2$ Content of Exhaust, vol. % | 9 | 8 | 7 |
| Condensate Xylene/H$_2$O, vol. ratio | 1.2 | 1.0 | 0.9 |
| Residence time, min. | 87 | 98 | 100 |
| Reaction Mixture: | | | |
| o-Phthalic Acid, wt. % | 90 | 87 | 90 |

The foregoing Comparative and Illustrative Examples indicate the o-phthalic acid yield by the weight percent o-phthalic acid in the reaction mixture on a water-free or water and acetic acid-free basis. In TABLE VI to follow there are shown more complete composition contents typical of products from oxidations such as Comparative Example III; Illustrative Examples I, II, III and VI; and the use of 20 grams acetic acid per gram mole of o-xylene and an aqueous solution of components of catalysis.

TABLE VI

Components of Reaction Mixture From Neat Oxidation of Liquid o-Xylene

| Component, Weight Percent | Comparative Example III | Illustrative Examples | | |
|---|---|---|---|---|
| | | I | II | III |
| Tolualdehyde | 0.61 | 0.12 | 0.80 | — |
| Benzoic Acid | 0.86 | 0.76 | 0.42 | 11.20 |
| o-Toluic Acid | 7.41 | 2.60 | 1.19 | 0.19 |
| 2-CBA* | 0.75 | 0.24 | 0.24 | 0.13 |
| Phthalide | 6.09 | 2.00 | 1.46 | 0.19 |
| o-Phthalic Acid | 70.10 | 81.2 | 84.6 | 73.5 |
| High Boilers | 2.79 | 1.18 | 1.29 | 0.83 |
| Water | 2.01 | 9.99 | 9.98 | 13.95 |
| Acetic Acid | — | 1.49 | — | — |

| Component, Weight Percent | Comparative Example III | Illustrative Examples | |
|---|---|---|---|
| | | IV | VI |
| Tolualdehyde | 0.61 | — | — |
| Benzoic Acid | 0.86 | 17.82 | 0.35 |
| o-Toluic Acid | 7.41 | 0.12 | 1.05 |
| 2-CBA* | 0.75 | 0.08 | 1.22 |
| Phthalide | 6.09 | 0.13 | 1.22 |
| o-Phthalic Acid | 70.10 | 71.0 | 71.0 |
| High Boilers | 2.79 | 0.79 | 2.17 |
| Water | 2.01 | 10.00 | 20.5 |
| Acetic Acid | — | — | 3.53 |

*"2-CBA" is 2-carboxybenzaldehyde.

The composition of the reaction mixture from Comparative Example III accounts for only about 90% of said mixture. It is our experience that such incomplete oxidations (low o-xylene conversions) have a low accountability for the oxygen-containing aromatic compounds.

The molar conversion of o-xylene in a one step oxidation using conditions of our prior batchwise or semicontinuous oxidation (Comparative Example III) and conditions of our present inventive process (e.g., Illustrative Example VI) are shown in TABLE VII.

TABLE VII

Molar Conversion of o-Xylene

| Compound Mole % | Comparative Example III | Illustrative Example VI |
|---|---|---|
| o-Phthalic Acid | 66 | 89.0 |
| o-Toluic Acid | 7.6 | 1.6 |
| 2-CBA | 6.2 | 1.9 |
| Benzoic Acid | 0.9 | 0.6 |
| Carbon Oxides | 6.3 | 6.5 |

It will be noted that the use of acetic or benzoic acid as a miscibility aid according to the present invention while permitting a more complete conversion of o-xylene to the desired product, o-phthalic acid and its precursors also permits tolerance of more than 7 to 8 weight percent water in accomplishing such higher conversion of o-xylene. This means that less precise control of water content of the reaction mixture is required, a substantial technical advantage.

The invention claimed is:

1. The preparation of o-phthalic acid by the air oxidation of liquid o-xylene at a temperature in the range of from 205° to 225° C. and a gauge pressure of from 28 to 30 kg/cm$^2$ in the presence of liquid ophthalic acid containing as solutes from 2 to 21 weight percent liquid water and for each gram mole of o-xylene from 1 up to 10 milligram atoms of cobalt, from 2 up to 20 milligram atoms of manganese and from 3 up to 40 milligram atoms of bromine derived from hydrogen bromide or elemental bromine as components of catalysis; the continuous operation comprising introducing into said liquid o-phthalic acid solution in a stirred oxidation zone in addition to air, o-xylene and said components of catalysis continuously and simultaneously in the relationship such that the air to xylene ratio provides at least 1.0 volume percent oxygen in the spent air portion of the exhaust from said zone and the ratio of components of catalysis to o-xylene are the 1 to 10 milligram atoms of cobalt, 2 to 20 milligram atoms of manganese and 3 up to 40 milligram atoms of bromine, the continuous and simultaneous introduction of from 5 up to 20 grams of acetic acid or benzoic acid per gram mole of o-xylene.

2. The method of claim 1 wherein for each gram mole of o-xylene introduced into the stirred oxidation zone there is introduced an aqueous solution of hydrogen bromide and cobaltous and manganous acetates to provide the requisite amounts of components of catalysis and from 7 to 11 grams of acetic acid.

3. The method of claim 1 wherein for each gram mole of o-xylene introduced into the stirred oxidation zone there is introduced an acetic acid solution of hydrogen bromide and cobaltous and manganous acetates containing from 42 to 65% acetic acid and 12 to 18% water by weight to provide the requisite amounts of components by catalysis.

4. The method of claim 1 wherein for each gram mole of o-xylene introduced into the stirred oxidation zone there are introduced from 10 up to 20 grams of benzoic acid per gram mole of o-xylene and an aqueous solution of hydrogen bromide and cobaltous and manganous acetates to provide the requisite amounts of the components of catalysis.

5. The method of claim 4 wherein the benzoic acid is dissolved in the o-xylene and the resulting solution introduced into the stirred reaction zone.

6. The method of claim 1 wherein for each gram mole of o-xylene introduced into the stirred oxidation zone there is introducted into the stirred oxidation zone the requisite components of catalysis and 4 to 9 grams of water as solutes in 10 to 20 grams of liquid benzoic acid.

* * * * *

UNITED STATES PATENT OFFICE
CERTIFICATE OF CORRECTION

Patent No. 4,211,881      Dated July 8, 1980

Inventor(s) Sydney G. Horsfield et al.

It is certified that error appears in the above-identified patent and that said Letters Patent are hereby corrected as shown below:

Patent reads:

| Col. | Line | |
|------|------|---|
| 5 | 1 | "liquor" and should read --liquid-- |
| 10 | 4 | "by' and should read --of--. |

Signed and Sealed this

Twenty-ninth Day of June 1982

[SEAL]

Attest:

GERALD J. MOSSINGHOFF

Attesting Officer      Commissioner of Patents and Trademarks